US00PP24395P3

(12) United States Plant Patent
Vitten et al.

(10) Patent No.: US PP24,395 P3
(45) Date of Patent: Apr. 22, 2014

(54) STRAWBERRY PLANT NAMED 'DRISSTRAWTHIRTYFOUR'

(50) Latin Name: *Fragaria×ananassa*
Varietal Denomination: DrisStrawThirtyFour

(75) Inventors: Matthias D. Vitten, Aptos, CA (US); Carlos D. Fear, West Malling (GB); Raúl Fernández Sánchez, Huelva (ES)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 58 days.

(21) Appl. No.: 13/573,332

(22) Filed: Sep. 11, 2012

(65) Prior Publication Data

US 2014/0075620 P1 Mar. 13, 2014

(51) Int. Cl.
*A01H 5/00* (2006.01)

(52) U.S. Cl.
USPC ..... Plt./208

(58) Field of Classification Search
USPC ..... Plt./208, 209
See application file for complete search history.

*Primary Examiner* — Kent L Bell

(74) *Attorney, Agent, or Firm* — Jondle Plant Sciences Division of Swanson & Bratschun, L.L.C.

(57) ABSTRACT

A new and distinct variety of strawberry plant named 'DrisStrawThirtyFour' particularly characterized by a very early harvest maturity, medium sized fruit, and very glossy fruit with sweet flavor, is disclosed.

1 Drawing Sheet

Genus and species: *Fragaria×ananassa.*
Variety denomination: 'DrisStrawThirtyFour'.

BACKGROUND OF THE NEW PLANT

The present invention relates to a new and distinct strawberry variety designated 'DrisStrawThirtyFour' and botanically known as *Fragaria×ananassa*. This new strawberry variety was discovered in Avitorejo, Spain in March 2010 and originated from a cross between the proprietary female parent 'RES 050-002' (unpatented) and the proprietary male parent '91P298' (unpatented). A single plant was selected for asexual propagation via tissue culture and vegetative cuttings in Avitorejo, Spain.

'DrisStrawThirtyFour' underwent further testing in Avitorejo, Spain for three years (2010-2012). The present invention has been found to retain its distinctive characteristics through successive asexual propagations via stolons and tissue culture.

Plant Breeder's Rights for this variety have not been applied for. 'DrisStrawThirtyFour' has not been made publicly available or sold more than one year prior to the filing date of this application.

SUMMARY OF THE INVENTION

The following are the most outstanding and distinguishing characteristics of this new cultivar when grown under normal horticultural practices in Avitorejo, Spain.

1. Very early harvest maturity;
2. Medium sized fruit; and
3. Very glossy fruit with sweet flavor.

DESCRIPTION OF THE PHOTOGRAPH

The accompanying color photograph shows typical specimens of the new variety at various stages of development. The colors shown are as true as can be reasonably obtained by conventional photographic procedures. The photograph is of whole plants approximately five to seven month-old and shows leaves, flowers, and fruit at various stages of development.

DESCRIPTION OF THE NEW VARIETY

The following detailed descriptions set forth the distinctive characteristics of 'DrisStrawThirtyFour'. The data which define these characteristics is based on observations taken in Avitorejo, Spain from 2010 to 2012. This description is in accordance with UPOV terminology. Color designations, color descriptions, and other phenotypical descriptions may deviate from the stated values and descriptions depending upon variation in environmental, seasonal, climatic, and cultural conditions. 'DrisStrawThirtyFour' has not been observed under all possible environmental conditions. The botanical description of 'DrisStrawThirtyFour' was taken from five to seven month-old plants. Color references are primarily to The R.H.S. Colour Chart of The Royal Horticultural Society of London (R.H.S.) (2007 edition). Descriptive terminology follows the *Plant Identification Terminology, An Illustrated Glossary, 2nd* edition by James G. Harris and Melinda Woolf Harris, unless where otherwise defined.

DETAILED BOTANICAL DESCRIPTION OF THE PLANT

Classification:
*Species.*—*Fragaria×ananassa.*
*Common name.*—Strawberry.
*Denomination.*—'DrisStrawThirtyFour'.

Parentage:
*Female parent.*—The proprietary variety 'RES 050-002' (unpatented).
*Male parent.*—The proprietary variety '91P298' (unpatented).

Plant:
*Height*.—15.5 cm.
*Diameter*.—34.7 cm.
*Number of crowns/plant*.—3.
*Habit*.—Flat globose.
*Density of individual plant*.—Open-sparse.
*Vigor* (*health and hardiness of plant*).—Weak.

Terminal leaflets:
*Size*.—Large. Length: 7.80 cm. Width: 6.34 cm. Length/width ratio: 1.2 (Longer than broad).
*Number of teeth/terminal leaflet*.—18.
*Shape of teeth*.—Rounded to crenate.
*Color*.—Upper surface: RHS N137B (Medium green). Lower surface: RHS 146B (Medium yellow-green).
*Shape in cross section*.—Slightly concave.
*Blistering*.—Medium.
*Glossiness*.—Strong.
*Number of leaflets*.—Three only.
*Shape*.—Oval.
*Base shape*.—Acute.
*Apex descriptor*.—Rounded.
*Variegation*.—Absent.
*Margin*.—Serrate.
*Margin profile*.—Flat (level with the leaflet blade).

Petiole:
*Length*.—Medium; 12.3 cm.
*Diameter*.—4.15 mm.
*Pubescence*.—Dense.
*Pose of hairs*.—Outwards — horizontal.
*Color*.—RHS 144A (Medium yellow-green).
*Bract frequency*.—2.

Petiolule:
*Length*.—9.89 mm.
*Diameter*.—1.88 mm.
*Color*.—RHS 144B (Medium yellow-green).

Stipule:
*Length*.—3.4 cm.
*Width*.—7.63 mm.
*Pubescence*.—Dense.
*Stipule anthocyanin coloration*.—Weak; RHS 141D (Light green).

Stolon:
*Number*.—Many.
*Average number of daughter plants per plant*.—30.
*Anthocyanin coloration*.—Weak.
*Thickness*.—Medium.
*Pubescence*.—Dense.

Inflorescence:
*Position relative to foliage*.—Level with.
*Number of flowers*.—Medium.
*Time of flowering* (*50% of plants at first flower*).—Very early.
*Flower size*.—Medium.
*Diameter*.—24.76 mm.
*Petals*.—Shape: Oval. Apex: Rounded. Base: Concavo — convex. Margin: Entire. Spacing: Overlapping. Length: 14.58 mm. Width: 14.42 mm. Length/width ratio: 1.0 (As long as broad). Petal number per flower: 6. Color (upper surface): RHS 155C (White).
*Calyx*.—Diameter: 56.53 mm. Diameter relative to corolla: Larger. Inner calyx diameter relative to outer: Smaller. Insertion of calyx: Set above fruit — raised. Pose of calyx segments: Clasping the fruit — downwards. Size of calyx in relation to fruit: Same size. Adherence of calyx: Weak.
*Sepal*.—Shape: Elliptical. Apex: Convex. Margin: Serrate. Length: 23.60 mm. Width: 10.18 mm. Sepal number per flower: 11.
*Receptacle color*.—RHS N144C (Medium yellow-green).
*Stamen*.—Present. Anther color: RHS 17B (Medium yellow-orange).
*Pedicel*.—Attitude of hairs: Upwards.

Fruiting truss:
*Length*.—Long; 22.3 cm.
*Diameter at base of truss*.—4.49 mm.
*Number of berries per fruiting truss*.—4.
*Attitude at first picking*.—Semi-erect.
*Color at base of truss*.—RHS 144A (Medium yellow-green).

Fruit:
*Relative fruit size*.—Medium.
*Length*.—40.73 mm.
*Width*.—35.96 mm.
*Length/width ratio*.—1.1 (As long as broad).
*Fruit hollow length*.—15.18 mm.
*Fruit hollow width*.—5.98 mm.
*Fruit hollow length/width ratio*.—2.5.
*Fruit hollow center* (*cavity*).—Small.
*Weight* (*per individual berry*).—24.8 g.
*Predominant fruit shape*.—Conical.
*Difference in shape between primary and secondary fruits*.—None or very slight.
*Evenness of fruit surface*.—Slightly uneven.
*Fruit skin color*.—RHS N34A (Dark orange-red).
*Evenness of fruit color*.—Slightly uneven.
*Fruit glossiness*.—Strong.
*Achenes*.—Insertion of achenes: Level with surface. Coloration (sunward side of berry): RHS 144C (Light yellow-green). Coloration (shaded side of berry): RHS 144A (Medium yellow-green). Number per berry: 376.0. Weight (weight of achenes divided by total # seed): 0.00053 g. Width of band without achenes: Absent or very narrow.
*Firmness of flesh* (*when fully ripe*).—Medium.
*Color of flesh* (*excluding core*).—RHS 31B (Medium orange-red).
*Color of core*.—RHS 31C (Light orange-red).
*Evenness of flesh color*.—Slightly uneven.
*Distribution of flesh color*.—Only marginal.
*Sweetness*.—Strong.
*Acidity*.—Weak.
*Texture when tasted*.—Fine.
*Type of bearing*.—Not everbearing — not remontant.
*Grams of fruit/plant*.—1223.9 g.
*Harvest interval*.—Mid December to late May.
*Harvest maturity*.—Very early.

Disease and pest resistance:
*Tetranychus urticae*.—Susceptible.
*Botrytis fruit rot*.—Moderately resistant.
*Powdery mildew*.—Moderately resistant.

Reaction to stress:
*Drought*.—Moderately susceptible.
*High temperatures*.—Moderately susceptible.
*Wind*.—Moderately resistant.

COMPARISON WITH PARENTAL AND COMMERCIAL VARIETIES

When 'DrisStrawThirtyFour' is compared to the female parent plant 'RES 050-002' (unpatented), 'DrisStrawThirtyFour' has earlier fruiting and is higher yielding than 'RES 050-002'.

When 'DrisStrawThirtyFour' is compared to the male parent plant '91P298' (unpatented), 'DrisStrawThirtyFour' has firmer fruit and higher vigor than '91P298'.

When 'DrisStrawThirtyFour' is compared to the commercial variety 'DrisStrawEight' (U.S. Plant Pat. No. 20,735), 'DrisStrawThirtyFour' has 3 crowns per plant, strong glossy leaves, and many stolons, whereas 'DrisStrawEight' has 2 crowns per plant, weakly glossy leaves, and a medium number of stolons. Additionally, 'DrisStrawThirtyFour' has medium sized fruit and an absent or very narrow band without achenes, whereas 'DrisStrawEight' has large sized fruit and a broad band without achenes.

When 'DrisStrawThirtyFour' is compared to the commercial variety 'DrisStrawSixteen' (U.S. Plant Pat. No. 22,247), 'DrisStrawThirtyFour' has medium leaf blistering, a flat terminal leaflet margin profile, and many stolons, whereas DrisStrawSixteen has strong leaf blistering, a revolute terminal leaflet margin profile, and few stolons. Additionally, 'DrisStrawThirtyFour' has berries with a small sized hollow center and strong sweetness, whereas 'DrisStrawSixteen' has berries with a medium sized hollow center and medium sweetness.

We claim:

1. A new and distinct variety of strawberry plant named 'DrisStrawThirtyFour' as described and shown herein.

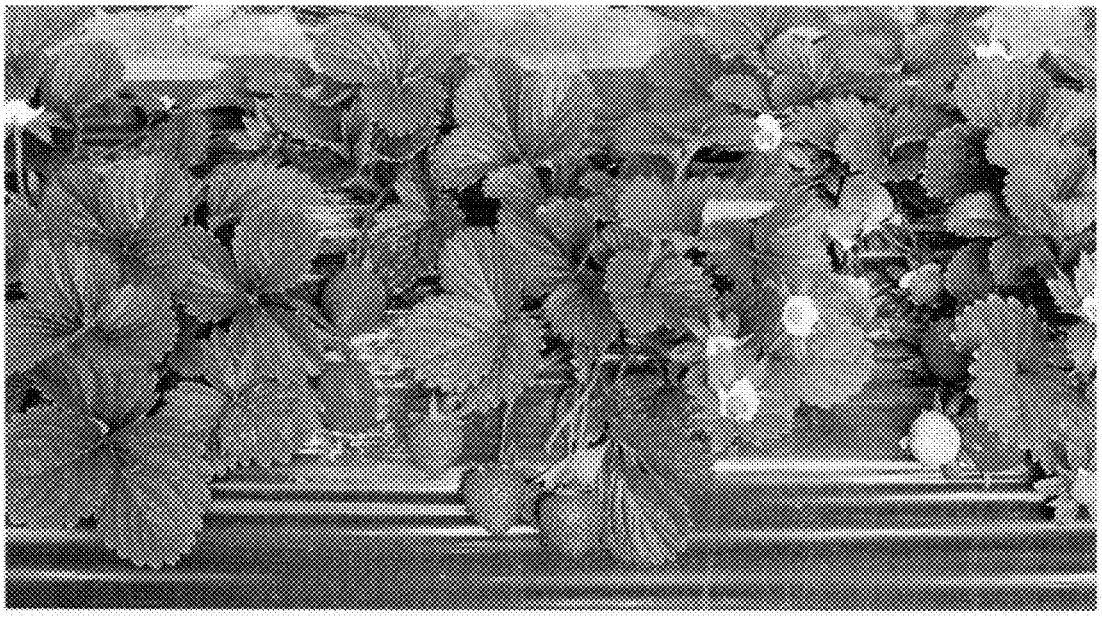

* * * * *